United States Patent [19]

Ito et al.

[11] Patent Number: 4,868,106
[45] Date of Patent: Sep. 19, 1989

[54] ANALYTICAL ELEMENT AND METHOD FOR DETERMINING A COMPONENT IN A TEST SAMPLE

[75] Inventors: Tsukasa Ito, Musashino; Satoshi Kawakatsu, Hachioji; Akira Onishi, Hino; Masayo Ishikawa, Tokyo, all of Japan

[73] Assignee: Konishiroku Photo Industry Co., Ltd., Tokyo, Japan

[21] Appl. No.: 919,676

[22] Filed: Oct. 16, 1986

[30] Foreign Application Priority Data

Oct. 17, 1985 [JP] Japan ................................. 60-229799
Oct. 17, 1985 [JP] Japan ................................. 60-229800

[51] Int. Cl.$^4$ .................. G01N 33/543; G01N 33/566
[52] U.S. Cl. .......................................... 435/7; 422/56; 422/57; 435/805; 436/501; 436/518; 436/524; 436/527; 436/528; 436/529; 436/530; 436/531; 436/800; 436/810; 436/827; 436/828
[58] Field of Search ............................ 435/7, 188, 805; 436/501, 518, 524, 527–531, 800, 810, 827, 828; 422/56, 57

[56] References Cited

U.S. PATENT DOCUMENTS

| | | | |
|---|---|---|---|
| 4,160,645 | 7/1979 | Ullman | 436/517 |
| 4,161,515 | 7/1979 | Ullman | 436/516 |
| 4,446,232 | 5/1984 | Liotta | 436/820 |
| 4,447,529 | 5/1984 | Greenquist et al. | 436/530 |
| 4,582,792 | 4/1986 | Kasahara et al. | 436/7 |
| 4,657,739 | 4/1987 | Yasuda et al. | 422/56 |

OTHER PUBLICATIONS

International Union of Biochemistry, *Enzyme Nomenclature*, Academic Press, New York, 1979, pp. 201 and 278.

Primary Examiner—Sam Rosen
Assistant Examiner—David A. Saunders
Attorney, Agent, or Firm—Finnegan, Henderson, Farabow, Garrett & Dunner

[57] ABSTRACT

Disclosed are an analytical element for determining a specific component A in a test sample, based on the specific reaction between said specific component A and a substance B capable of binding specifically to said specific component A, by the use of a labelled material L comprising a label capable of providing a signal and said specific component A or comprising a label capable of providing a signal and a substance C capable of binding specifically to said specific component A, characterized in that said element has a porous reaction layer formed by the use of a mixture containing (a) a carrier having said substance B immobilized thereon and (b) a carrier having an absorbing substance D capable of binding specifically to said labelled material L which has not bound to said substance B or to said specific compound A, to thereby modulate said signal, and an analytical method employing the same.

26 Claims, 3 Drawing Sheets

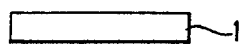
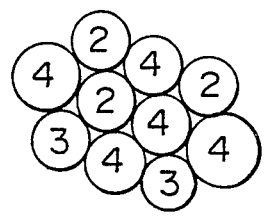
FIG. 1          FIG. 2
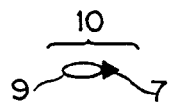
FIG. 3-a
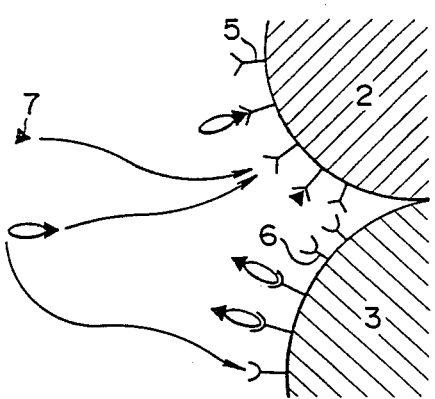
FIG. 4-a

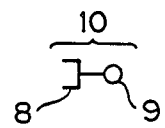
FIG. 3-b
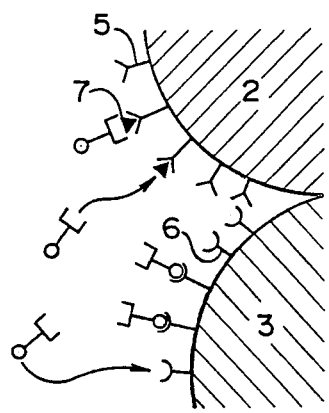
FIG. 4-b
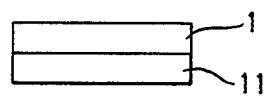
FIG. 5
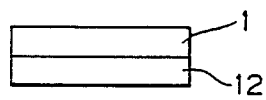
FIG. 6
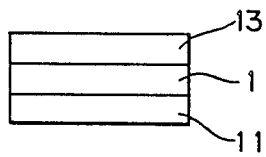
FIG. 7

ANALYTICAL ELEMENT AND METHOD FOR DETERMINING A COMPONENT IN A TEST SAMPLE

BACKGROUND OF THE INVENTION

This invention relates to an analytical element for measuring a minute amount of a component in a fluid sample, particularly to an analytical element for analysing a specific minute amount of a component in a biological fluid sample, and an analytical method employing the same.

As a method for detecting a substance contained in an extremely minute amount in a biological fluid sample, various analytical methods have been developed. The analytical methods are based primarily on immune reactions as their principles. While various measurement methods by use of the above principle have been developed, immunoassay is known as the method with the highest precision.

As the immunoassay, radioimmunoassay has been widely employed since Berson and Ylow successed in 1958 in assay of insulin in a serum by use of bovine insulin labelled with radioactive iodine and an anti-insulin antibody in a serum of a diabete patient.

Hereafter, as the labelling compounds, various compounds other than radioisotopes have been developed. As other labelling compounds, there may be included, for example, enzymes, enzyme substrates, coenzymes, enzyme inhibitors, bacteriophages, circulating reactants, metals and organic metallic complexes, organic prosthetic groups, chemiluminescent reactants and fluorescent molecules, etc.

As one of the important problems in technology concerning the above immunoassay, there is a problem how to separate a substance which has been bound (hereinafter abbreviated as B) from a substance which has not been bound (hereinafter abbreviated as F) (hereinafter abbreviated as B/F separation).

In the prior art, various methods have been developed for solving the problems in immunoassay (for example, see Japanese Unexamined patent publication Nos. 38619/1978, 79024/1978, 90859/1980, 67860/1982, 200862/1982, 18167/1983, 77356/1984 and 170768/1984).

However, these methods had the drawbacks that B/F separation is incomplete, that there is a problem with respect to reliability of signal due to much noise, that a substance which can be assayed is limited to low molecular weight substances, etc.

On the other hand, in wet chemistry, there has been developed an immunoassay according to the competitive method by use of a immobilizing phase (see, for example, Japanese Unexamined patent publication Nos. 209994/1983 and 202064/1984). However, in those immunoassays, since the whole enzyme activity is assayed without discrimination between both immobilizing phases, no satisfactory result can be obtained with respect to sensitivity, precision and reproducibility owing to the problems such as backgroun or noise.

On the other hand, in dry chemistry, there has been developed an immunoassay by use of a second antibody (see Japanese Unexamined Patent Publication Nos. 82766/1982 and 82767/1982). However, these techniques involved such problems to be improved that the operation is cumbersome and that a technique for performing spreading with good reproducibility is required, etc. Further, in the invention disclosed in Japanese Unexamined Patent Publication No. 34155/1984, a method by use of an unbound product housing sheet is disclosed. However, even according to this method, the above mentioned problems will occur when measurement is to be performed with the sheet for reaction being contacted with the unbound product housing sheet, and it is also cumbersome to separate the both sheets during measurement, which will particularly become an obstacle when the measurement is automated.

The present invention has been accomplished for the purpose of improving the drawbacks of the prior art as described above, and its object is to provide an analytical element, which is applicable for substances of a broad range of molecular weights (100 to 5,000,000) as the subject to be measured, by performing the B/F separation in a single phase, and can quantitatively determine a specific component in a fluid sample with excellent sensitivity, precision and reproducibility according to a simple operation.

SUMMARY OF THE INVENTION

The present invention relates to an analytical element for determining a specific component A in a test sample, based on the specific reaction between said specific component A and a substance B capable of binding specifically to said specific component A, by the use of a labelled material L comprising a label capable of providing a signal and said specific component A or comprising a label capable of providing a signal and a substance C capable of binding specifically to said specific component A, characterized in that said element has a porous reaction layer formed by the use of a mixture containing (a) a carrier having said substance B immobilized thereon and (b) a carrier having an absorbing substance D capable of binding specifically to said labelled material L which has not bound to said substance B or to said specific compound A, to thereby modulate said signal, and an analytical method employing the same.

BRIEF DESCRIPTION OF THE DRAWINGS

FIG. 1 and FIGS. 5 to 10 are each schematic sectional view showing one embodiment of the analytical element of the present invention;

FIG. 2 is an enlarged view of FIG. 1;

FIGS. 3-a and 3-b are each schematic sectional view of a labelled material;

FIGS. 4-a and 4-b are each schematic illustration of the present invention;

DETAILED DESCRIPTION OF THE INVENTION

Figure 8:
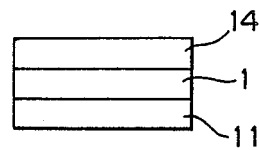

The fluid sample which can be used in the present invention may include all forms of solutions and colloid solutions, preferably fluid samples derived from organisms, namely blood, plasma, serum, cerebrospinal fluid, saliva, amnionic fluid, milk, urine, sweat, broth, etc., particularly preferably blood and serum.

The specific component A in the fluid sample which can be measured by the present invention is a substance or a group of substances of which existence or amount in the fluid sample can be measured and for which a substance capable of binding specifically to its component is available, as exemplified by the substances or groups of substances set forth in the following Table 1.

TABLE 1

(Proteins)
Albumin; Prealbumin;
$\alpha_1$-acid glycoprotein; $\alpha_1$-Glycoprotein;
Tryptophan deficient; $\alpha_1$-Lipoprotein;
$\alpha_1$-Antitrypsin; $\alpha_2$-Glycoprotein;
$\alpha_2$-Lipoprotein; $\beta$-Lipoprotein;
$\beta$-Glycoprotein; C-reactive protein;
Fibrin-eliminated product;
Fibrinogen; Immunoglobulin A;
Immunoglobulin D; Immunoglobulin E;
Immunoglobulin G; Immunoglobulin M;
Haptoglobin; Hemoglobin;
Ceruloplasmin; Cholinesterase;
Hemopexin; Mycoglobin;
Rheumatoid factor; Thyroxine-binding globulin;
Transferrin; Transcortin;
Plasminogen; Specific antibody;
Agglutinating factor; Complementary factor;

(Peptide hormones)
Adrenocorticotropin; Meth- and leu-enkephalin;
(ACTH);
Thyroxine; Triiodothyronine;

(Proteohormones)
Chorionic gonadotropin; Chorionic thyrotropin;
Glucagon; Insulin;
Neuron growth factor; Parathyroid hormone;
Placental lactogens; Prolactin;
Proinsulin; Relaxin;

(Histiohormones)
Secretin; Gastrin;
Angiotensin I and II; Human placental lactogen;

(Peptidohormones from posterior lobe of hypophysis)
Oxytocin; Vasopressin;
Releasing factor (RF)
CRF, LRF, TRF, somatotropin-RF, GHF, FSH-RF, RIF, MIF (Carcinomatous markers)
Carcinoembryonic antigen; Gangliosides;
$\alpha$-fetoprotein; Basic fetoprotein;
Pancreatic carcino-embryonic antigen; Pregnancy specific $\beta_1$-glycoprotein;
TPA; Ferritin;
$\beta_2$-microglobulin; Myeloma protein;
Astroprotein; Prostatic antigen;
Squamous cell carci-noma-associated antigen; CA19-9;

(Surface markers of microorganism)
Bacterial antigen; Mycological antigen;
Parasitic antigen; Viral antigen;

Alkaloid medicines)
Benzoylecgonine; Cocaine;
Codeine; Dextrometrophan;
Heroin; Liserg acid;
Morphine; Quinidine;
Quinine;
and metabolites of these;

(Aminoglucoside medicines)
Amycacin; Gentamicin;
Kanamycin; Neomycin;
Dopramycin;
and metabolites thereof;

(Antibiotic medicines)
Actinomycetin; Karomycin;
Chloramphenicol; Chloromycetin;
Chlorotetracycline; Erythromycin;
Oxytetracycline; Penicillin;
Polymixine B; Teramycin;
Tetracycline; Streptomycin;
and metabolites thereof;

(Barbituric acid salt medicines)
Diphenylhydantoin; Ethosuximide;
Phenobarbital; Primidone;
Secovarbital;
and metabolites thereof;

TABLE 1-continued (Marihuana derivatives)
Canabinol; Tetrahydrocanabinol;
and metabolites thereof;

(Metabolites)
Galactose; Phenylpyruvic acid;
Porphyrin; Spermine;

(Various medicines)
Amitriptilin; Anticholinergic medicine;
Antihistamine; Athoropin;
Butyrophenone; Caffeine;
Carbamazepin; Chlorobromadine;
Epinefurine; Gliseorofuluin;
Imipuramin; L-dopa;
Lidocaine; Meperidine;
Meprobamate; Metadone;
N—acetylbrocainamide; Narceine;
Nortripthilin; Oxazepam;
Papaverine; Brocainamide;
Propanolol; Prostaglandin;
Tegletol; Theophylline;
Serotonin; Barpron acid;
and metabolites thereof;

(Vitamins)
Biotin; Folic acid;
Thiamin; Vitamin A;
Vitamin $B_2$; Vitamin $B_6$;
Vitamin $B_{12}$; Vitamin C;
Vitamin D; Vitamin E;
Vitamin K;

(Steroids)
Adrenocorticol; Androgens;
Steroid;
Bail acid; Digoxine;
Digoxigenine; Diethylstylbestrol;
Estrogen; Gestrogen;

(Agricultural chemicals)
Biphenyl halide; Phosphate ester;
Thiophosphate;
and metabolites thereof.

As the substance B capable of binding specifically to the specific component A in the fluid sample which can be used in the present invention, there may be included antibodies, antigen, lectin, protein A, inhibitors of specific enzymes, etc., depending on a substance to be measured. It is particularly preferred that the binding reaction between said specific component and said binding substance is an antigen-antibody reaction. The antibody to be used in the present invention is not particularly limited in its sources, and it is possible to use an antiserum or ascite derived from mammals, etc., immunized by administration of an antigen without purification or after purification by the methods known in the art such as the sodium sulfate precipitation method, the ammonium sulfate precipitation method, the gel filtration method by Sephadex gel, the ion exchange cellulose chromatography method, the electrophoretic method, etc. (see "Immunochemistry" edited by Shunsuke Migita, P. 74–88, published by Nakayama Shoten).

Alternatively, a monoclonal antibody may be prepared by obtaining a hydridoma from spleen cells and myeloma cells of a mammal, etc. (e.g. mouse) immunized with an antigen.

Also, these antibodies may be respective fractions of IgG, IgM, IgA, IgD, IgE, or alternatively these antibodies may be subjected to enzyme treatment to form active antibody fragments such as Fab or Fab'. Further, these antibodies may be used either singly or as a combination with a plurality of antibodies.

When an antibody or an antigen is used as the substance B capable of being specifically bound to the specific component A in a fluid sample, the measuring principle of the analytical element of the present invention belongs to immunoassay. While the analytical element of the present invention can be particularly preferably used in immunoassay, it is not limited to immunoassay, but various applications are possible as can be clearly seen from the contents as described above.

The label applicable for the present invention may include, for example, enzymes, enzyme substrates, substances which change the activities of enzymes or enzyme precursors (enzyme inhibitors, coenzymes, prosthetic groups, substances capable of activating enzyme precursors, etc.), enzyme precursors, apoenzymes, fluorescent substances, etc., of which typical examples are set forth in the following Table 2. More preferably, enzymes and fluorescent substances disclosed in Table 2 can be used. (The signals caused by these labels are described hereinafter).

1. Enzymes
EC 1.1.1.1. Alcohol dehydrogenase
1.1.1.6. Glycerol dehydrogenase
1.1.1.27. Lactate dehydrogenase
1.1.1.37. Malate dehydrogenase
1.1.1.49. Glucose-6-phosphate dehydrogenase
1.1.3.4. Glucose oxidase
1.1.3.9. Galactose oxidase
1.2.1.12. Glyceraldehyde-3-phosphate dehydrogenase
1.2.3.2. Xanthine oxidase
Luciferase
1.4.3.2. L-amino acid oxidase
1.4.3.3. D-amino acid oxidase
1.6.4.3. Dihydrolipoamidoreductase ($NAD^+$) (diahorase)
1.7.3.3. Urate oxidase
1.11.1.6. Catalase
1.11.1.7. Peroxidase
2.7.1.1. Hexokinase
2.7.1.2. Glucokinase
2.7.1.15. Ribokinase
2.7.1.28. Tryokinase
2.7.1.40. Pyruvate kinase
2.7.5.1. Phosphoglucomutase
3.1.1.7. Choline esterase
3.1.1.8. Pseudocholinesterase
3.1.3.1. Alkali phosphatase
3.1.3.2. Acid phosphatase
3.1.3.9. Glucose-6-phosphatase
3.1.3.11. Fructosediphosphatase
3.1.4.1. Phosphodiesterase
3.1.4.3. Phospholipase C
3.2.1.1. α-Amylase
3.2.1.2. β-Amylase
3.2.1.4. Cellulase
3.2.1.17. Muramidase
3.2.1.18. Neuraminidase
3.2.1.21. β-Glycosidase
3.2.1.23. β-Galactosidase
3.2.1.31. β-Gluculonydase
3.2.1.35. Hyarulonidase
3.2.2.5. DPNase
4.1.2.13. Aldolase
4.2.1.1. Carbonic anhydrase
5.3.1.1. Tryose phosphate isomerase
6.3.4,14. Biotin carboxylase
6.4.1.1. Pyruvate carboxylase
6.4.1.2. Acetyl-CoA carboxylase
6.4.1. Propionyl-CoA carboxylase, etc.

2. Substrates
P—nitrophenyl-β-D-galactoside
O—nitrophenyl-β-D-galactoside
4-Methylumbelliferone-β-D-galactoside
P—nitrophenylphosphate
Cortisol-21-hemisuccinate umbelliferone conjugate
Luminol
Isoluminol
N—(4-aminobutyl)-N—ethyl isoluminol hemisuccinamide
N—(6-aminohexyl)-N—ethyl isoluminol N—(4-aminobutyl)-N—ethyl isoluminol lucigenine
Acridinium phenyl carboxylate
Rofine
Pyrogallol
Gallic acid
Siloxine
Bis(2,4,6-trichlorophenyl)oxalate
and derivatives thereof 3. Enzyme inhibitors
Physostigmine
Methionine sulfoxymine
Wildfire toxin
Blue dextran
O—dianisidine-cellulose
O—dianisidine-dextran
2-Propinylamine
2-Chloroallylamine
Phenylglycine
P—nitrophenylglycine
Aminoacetonitrile
2-Amino-3-hydroxypropyl-1,3'-carboxy-3'-amino-1'-propenyl-1 ether
L-2-amino-4-methoxy-trans-3-butene acid
Ethanolamine o-sulfate
Albidiine
Azacerin
Diazooxonolleucine
Diazooxonoanolvaline
$\Delta^3$-7-Aminosefalospo phosphate
Mimosine
2-Amino-4-pentyne acid
2-Amino-4-chloro-4-pentene acid
3,3-Dichloroalanine
3,3,3-Trichloroalanine
D-cycloserine
2-Hydroxyl-3-butyne acid
N,N—trimethyl-2-propinylamine
β-Aminopropionitrile
2-Bromoethylamine
3-Decinoyl-N—acetylcisteamine
2,3-Decadienoyl-N—acetylcisteamine
β-Chloro-L-alanine
L-serine-o-sulfate
β-Fluoroalanine
L-vinylglycine
D-vinylglycine
Propargylglycine
Gabacrine
5-Nitro-L-norvaline
N—benzyl-N—methyl-2-propinylamine
3-Dimethylamino-1-propyne
Glycerol
Diisopropylphosphorofluoride
Phenylmethanesulfonylfluoride
Kuraburane acid
Alobrynol
Butyl tin
Iodoacetic acid
Iodoacetamide
Bestathine
Pyridoxalphosphoric acid
Hydrazine and its derivatives
Nitrofuran and its derivatives
Nitrobenzene and its derivatives
Purine derivatives
Chelating agents
Heavy metal ions
Mercury compounds, etc.

4. Coenzyme, prosthetic group
FAD (flavine adenine dinucleotide)
FMN (flavine mononucleotide)
Heme
S—adenocilmethionine
THF (tetrahydrofolic acid)
TPP (thiamine diphosphate)
CoA (coenzyme A)
UDP-Glc (uridine diphosphate glucose)
PLP (pyridoxal phosphate)
ATP (adenosine triphosphate)
Biotin
CoI (nicotinamidoadenine dinucleotide)
CoII (nicotinamidoadenine dinucleotide phosphate)

-continued

Adenosylcobalamin
Methylcobalamin
CoM (2,2'-dithiodiethane sulfonate)
CoQ (ubiquinone)

5. Apoenzymes

Apoglutathione reductase
Apocytochrome reductase
ApoNADPH dehydrogenase
Apoglucose oxidase
Apolipoamide dehydrogenase
Apopyridoxine phosphate oxidase
Apoperoxidase
Apocytochrome C
Apoxanthine oxidase
Apo-yeast lactate dehydrogenase
Aposarcosine oxidase
Apo-p-hydroxybenzoate hydroxylase
Apoacyl-CoA dehydrogenase
Apo-dihydrolipo acid dehydrogenase
Aposuccinate dehydrogenase
Apohomosisteinemethyl transferase
Apoglutamate formyl transferase
Apotransketolase
Apocholineacetyl transferase
Apoglycogen synthase
Apoalanineamino transferase
Apohexokinase 6. Substances capable of activating enzyme precursors Enteropeptidase
Streptokinase
Protein kinase
Various proteases of enzyme precursors 7. Enzyme precursors Tripsinogen
Chymotripsinogen
Procolipase
Prophospholipase
Prorenin
Procarboxypeptidase A
Procarboxypeptidase B
Quininogen
Proelastase
Angiotensinogen
Proinsulin
Proparathyroid hormone
Proglucagon
Procollagen (soluble)
Agglutinating factor XI, XII, XIII
Procollagenase
Prococonase
Prekallikrein
Pepsinogen
Plasminogen
Fibrinogen
Prothrombin
Plasminogen proactivator
Proacrodine 8. Fluorescent substances Fluorescein isothiocyanate (FITC)
Tetramethylrhodamine isothiocyanate (TRITC)
Rhodamine B isothiocyanate (RBITC)
Lissamine Rhodamine-B200 sulforyl chloride (RB200SC)
Umbelliferone
4-Methylumbelliferone (4MU)
Fluorescein thiocarbamyl (FTC)
Fluoresein thiocarbamyl-diphenylglycine (FTC-DPG)
Tetramethylrhodamine (TMR)
5-[(4,6-dichlorotriadin-2-yl)-amino]fluorescein
Dimethylaminonaphthalene-5-sulfonyl chloride (DNS-Cl)
Fluorum
2-Methoxy-2,4-diphenyl-3(2H)-furanone (MDPF)
7-Chloro-4-nitrobenzo-2-oxa-1,3-diazole (NBD-Cl)
1-Anilino-8-naphthalenesulfonic acid (ANS)
N—(3-pyrene)-maleimide (NPM)
N—(7-dimethylamino-4-methyl-2-oxy-3-chloromethyl)-maleimide (DACM)
N—(p-2-benzimidazoyl-phenyl)-maleimide (BIPM)
Anthraceneisothiocyanate
Fluoroanthylmaleimide (FAM)

-continued

Various chelates containing rare earth elements and derivatives thereof

The analytical method according to the present invention may be applied to both of the so-called competitive reaction method and sandwich method. The labelled material in the competitive reaction method (hereinafter abbreviated as $L_{comp}$) and the labelled material in the sandwich method (hereinafter abbreviated as $L_{sand}$) differ to some extent from each other. In the so-called competitive reaction, the labelled material $L_{comp}$ in which the specific component A or its analogue (hereinafter called comprehensively as "substance E") and a label are bound to each other refers comprehensively to substances which can be specifically bound by the substance B capable of binding specifically to the specific component A as described above, in the same manner or similarly as said specific component, and also has the above mentioned label bound to the specific component A directly or indirectly by chemical means, etc., while maintaining its ability to generate a signal. Practically, it can be obtained by chemically binding the above mentioned label to said specific component or a substance having the antigenic determinant common to said specific component according to the known method. On the other hand, in the sandwich method, the labelled material $L_{sand}$ refers to a substance in which the above label is bound to a substance C which can be specifically bound to the component A directly or indirectly by chemical means, etc., without deterioration of capability thereof to give a signal.

More specifically, these labelled materials can be prepared by referring to the method as described in "Enzyme Immunoassay (2nd edition)" edited by Eiji Ishikawa, Tadashi Kawai, Kiyoshi Miyagawa (published by Igaku Shoin, 1978) of "Clinical Pathology" Special Extra Vol. 53 "Immunoassay for Clinical Test—Technology and Application—" edited by Society of Clinical Pathology of Japan (published by Society of Clinical Pathology Publication, 1983). In the following, description is made by referring to specific examples in case where the label is an enzyme, by which the present invention is not limited.

(1) The method in which said substance E and said enzyme are allowed to react with a crosslinking agent as shown below.

1 2,4,6-Trichloro-1,3,5-triazine
2 4,4'-Difluoro-3,3'-dinitrodiphenylsulfone
3 Toluene-2,4-diisocyanate
4 N,N'-dicyclohexylcarbodiimide
5 1-(3-dimethylaminopropyl)-3-ethylcarbodiimide
6 Bisdiazo-o-dianisidine
7 Glutaraldehyde, etc.

(2) When at least one of said substance E and said enzyme has a sugar chain, the method in which said sugar chain is treated with periodic acid and an aldehyde group formed is allowed to react with an amino group of the partner substance to be bound (if necessary, for inhibiting formation of unnecessary bondings during the periodic acid treatment, there may be taken a measure such as pretreating said substance E or said enzyme with 1-fluoro-2,4-dinitrobenzene, etc., or controlling the pH in the periodic acid treatment reaction to 4–5, or stabilizing by treatment of a bonding based on a Schiff base formed between said substance E and said enzyme, with sodium borohydride, ethanolamine, etc.).

(3) When said substance E and said enzyme has a thiol group, or forms a thiol group by reduction, etc., or thiol roups can be introduced by treatment with an appropriate compound, a method in which various crosslinking agents known as the maleimide reagent are allowed to react with said thiol groups.

Here, examples of the compounds into which a thiol group can be introduced include the following:
1. S-acetylmercaptosuccinic acid anhydride
2. Methyl-3-mercaptopropioneimidate
3. Methyl-4-mercaptobutylimidate
4. 2-Iminothiolane
5. 3-(2'-dithiopyridyl)propionic acid N-hydroxysuccinimide ester
6. Methyl 3-(4'-dithiopyridyl)propionimidate, etc.

On the other hand, examples of the above mentioned maleimide reagent include the following:
1. N,N'-o-phenylenedimaleimide
2. N,N'-p-phenylenedimaleimide
3. N,N'-m-phenylenedimaleimide
4. N,N'-oxydimethylenedimaleimide
5. N-succinimidyl-N-maleimide acetate
6. N-succinimidyl-4-(N-maleimide)butyrate
7. N-succinimidyl-5-(N-maleimide)heptanoate
8. N-succinimidyl-6-(N-maleimide)hexanoate
9. N-succinimidyl-4-(N-maleimidemethyl)cyclohexane-1-carboxylate
10. N-succinimidyl-m-(N-maleimide)benzoate
11. N-succinimidyl-p-(N-maleimidephenyl)-4-butyrate
12. N-sulfosuccinimidyl-4-(N-maleimidemethyl)cyclohexane-1-carboxylate
13. N-sulfosuccinimidyl-m-(N-maleimide)benzoate
14. N-sulfosuccinimidyl-p-(N-maleimidephenyl)-4-butyrate
15. N-succinimidyl-4-(N-maleimidemethyl)benzene-1-carboxylate, etc.]

(4) A method in which pyridyl disulfide groups are introduced into said substance E or said enzyme, which are then allowed to react with thiol groups introduced into or existing originally in the partner compound to be bound.

[Pyridyl disulfide groups may be introduced by treatment with 3-(2'-dithiopyridyl)propionic acid N-hydroxysuccinimide ester or methyl-3-(4'-dithiopyridyl)propionimidate, etc., and for introduction of thiol groups, the method as described in the item (3) can be utilized.]

(5) When said substance E and said enzyme have thiol groups or can form thiol groups by reduction, etc., or thiol groups can be introduced thereto by treatment with an appropriate compound, a method in which the thiol groups in one of the above substances are converted to pyridyl disulfide groups, which are then allowed to react with the thiol groups of the partner substance to be bound. [Conversion of thiol groups to pyridyl disulfide groups can be effected with 4,4'-dithiodipyridine, etc.]

(6) A method in which amino groups or thiol groups existing in or introduced into said substance E and said enzyme are allowed to react with p-benzoquinoline.

(7) A method in which monoiodoacetic acid N-hydroxysuccinimide ester is allowed to react with thiol groups existing in or introduced into said substance E and said enzyme.

(8) A method in which an antibody to said substance E, an antibody to said enzyme, and an antibody capable of specifically binding commonly to the former two antibodies are reacted.

(9) A method in which one of said substance E and said enzyme is bound to avidin and the other to biotin, and the both are bound by biotin-avidin bonding.

Among these methods, the glutaraldehyde method, the periodic acid method (Nakane method) and the maleimide method can be particularly preferably used.

Further in the sandwich method, the substance C which can be specifically bound to the specific component A to be used for the labelled material $L_{sand}$ can be selected from those described above as to be used for the substance B capable of binding specifically to the specific component A immobilized on the substrate, provided that the substances B and C can be bound to different moieties in one molecule of said specific component A, respectively, at the same time.

The absorbing substance D to be used in the present invention, namely the substance D which can be bound specifically to the above mentioned labelled material C to extinguish or diminish a signal caused by said label, should be selected corresponding to the label employed, and may include, for example, the substances as shown below.

1. When the label is an "enzyme":
Signal caused by label
    Decrease of substrate and increase of product by said enzyme activity, radiation of energy and changes caused by them.
Preferable absorbing substance D
    Inhibitor against said enzyme (an inhibitor corresponding to said enzyme can be selected from those set forth in Table 2);
    Antibody to said enzyme, which can be bound to oxygen to exert an influence on its activity.

2. When the label is an "enzyme substrate":
Signal caused by label
    Increase of a product formed by the reaction of said substrate with an enzyme added in the analytical element, radiation of energy and changes caused by them.
Preferable absorbing substance D
    Antibody to said substrate, which can be bound to the substrate to inhibit said enzymatic reaction;
    Enzyme which can incorporate said substrate as irreversible inhibitor;
    Enzyme for which said substrate is a substrate, and which does not generate a signal to be detected by the reaction therebetween.

3. When the label is a "coenzyme" or a "prosthetic group":
Signal caused by label
    Decrease of substrate and increase of product by the reaction of an enzyme for which said label added in the analytical element is required, and changes caused by them.
Preferable absorbing substance D
    Antibody to said label, which can be bound to said label to exert an influence on its activity;
    Substance which absorbs or consumes said label but does not generate a signal to be detected by its activity.

4. When the label is an "apoenzyme":
Signal caused by label
    Said label does not generate a signal as such. Enzyme activity can be exhibited when the label is bound to an absorbing substance as mentioned below, whereby decrease of substrate and increase of product by its activity and changes caused by them can be measured.
Preferable absorbing substance D
    Prosthetic group capable of exhibiting enzyme activity of said label (prosthetic group corresponding to said label can be selected from those as exemplified in Table 2).

5. When the label is a "substance capable of activating an enzyme precursor":
Signal caused by label Decrease of substrate and increase of product by the activity obtained by activation of an enzyme precursor added in the analytical element by said label, and changes caused by them.
Preferable absorbing substance D Antibody to said substance, which can be bound to said substance to exert an influence on its activity;

When said substance is an enzyme, its inhibitor.

6. When the label is an "enzyme precursor":
o Signal caused by label

Said label does not generate a signal as such. After once bound to an absorbing substance mentioned below, a part of the molecule is cleaved to exhibit an enzyme activity, and decrease of substrate and increase of product by its activity and changes caused by them can be measured.
o Preferable absorbing substance D Substance which can exhibit enzymatic activity of said label.

7. When the label is a "fluorescent substance":
o Signal caused by label

Fluorescence emitted when said fluorescent substance is irradiated with an exciting light.
o Preferable absorbing substance D Antibody to said label and its derivative, which can change the fluorescent wavelength and intensity of said label.

Specific examples of various absorbing substances as mentioned above are well known to those skilled in the art and need not disclosed here again, but typical examples are set forth below for better understanding of the present invention.

As the combination of the enzyme and the inhibitor which can be used in the present invention, there may be included aryl mercury derivative and SH enzyme (glucose oxidase, choline oxidase, glycolate oxidase, glycerol-3-phosphate dihydrogenase, malate dehydrogenase, glutarate dehydrogenase, lactate dehydrogenase, glucose-6-phosphate dehydrogenase, etc.), isophthalic acid derivative and glutarate dehydrogenase, α-amylase and amylase inhibitor, esterase and bestatin, a biotin enzyme (pyruvate carboxylase, acetyl Co-A carboxylase, propionyl-CoA carboxylase, methylmalonyl-CoA carboxylase, etc.) and avidin, peroxidase and o-dianidine-dextrane, lactate oxidase and 2-hydroxyl-3-butyne acid, monoamine oxidase and N,N-trimethyl-2-propynylamine or β-aminopropionitrile, etc., and further it is preferable to use the combination of enzyme and inhibitor as described or referred to in Journal of the American Chemical Society (J. Am. Chem. Soc) Vol. 80, P. 456 (1958); ibid. Vol. 82, P. 596 (1960); Accounts of Chemical Research (Acc. Chem. Res) Vol. 9, P. 313 (1976); Science, Vol. 185, P. 320 (1974); Kagaku Kogyo (Chemical Industry) (1985), P. 21 (1985), etc.

The above-mentioned aryl mercury derivative is an organic mercury compound represented by general formula: $R(HgX)_n$.

In the general formula, R represents a benzene or naphthalene ring and it may have a substituent. The substituent may include a halogen atom (F, Cl, Br, I),

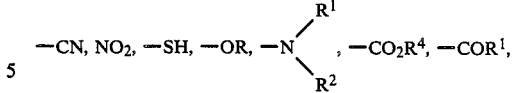

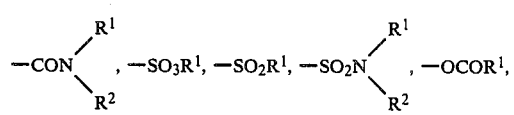

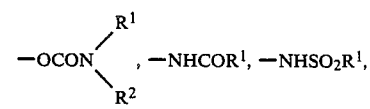

an alkyl group and a phenyl group which may have a substituent, etc; and $R^1$ and $R^2$ each represent an alkyl group and a phenyl group which may have a substituent, and a hydrogen atom. The number of the substituent on a benzene or naphthalene ring may be 7 or less, preferably 3 or less. X represents a monovalent acid group. n is an integer of 1 or 2.

The specific example of the aryl mercury derivatives in this invention will be shown below.

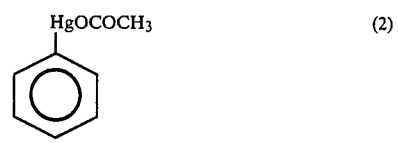

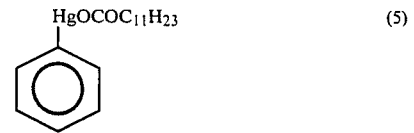

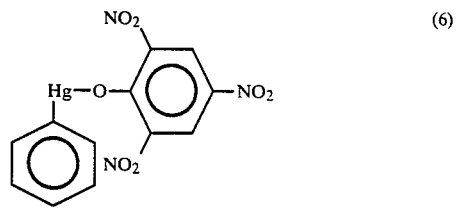

-continued
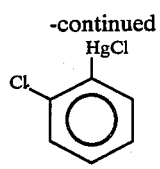 (7)
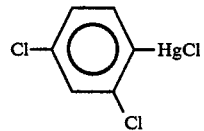 (8)
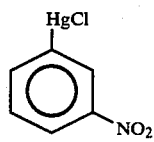 (9)
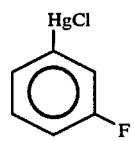 (10)
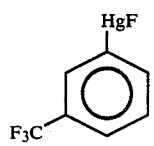 (11)
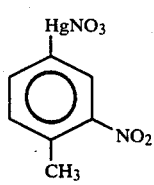 (12)
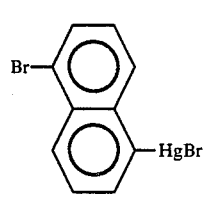 (13)
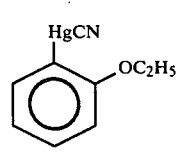 (14)
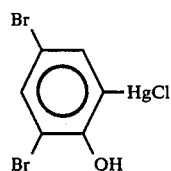 (15)
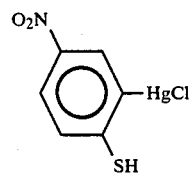 (16)
-continued
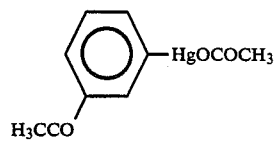 (17)
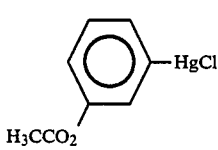 (18)
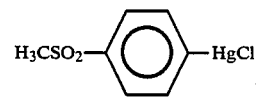 (19)
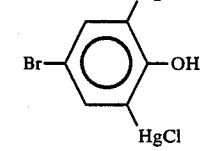 (20)
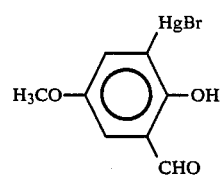 (21)
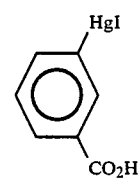 (22)
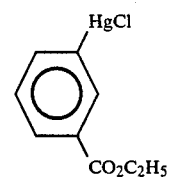 (23)
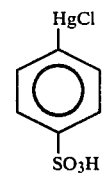 (24)
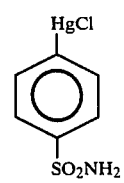 (25)

-continued

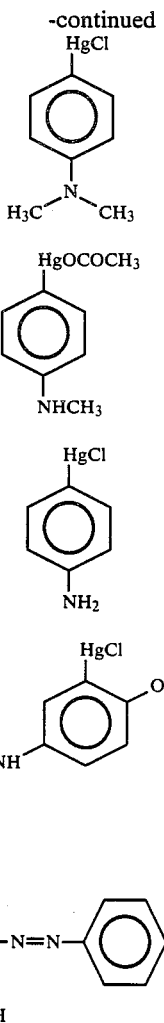

Other aryl mercury derivatives are described in detail on pages 1347 to 1424 of Beilsteins Handbuch der Organischen Chemie (fourth edition), vol. XVI, the second supplement) and these derivatives can be synthesized according to the method described in the above literature.

The porous reaction layer which constitutes the main part of the present invention is formed by use of a mixture containing the carriers represented by the above (a) and (b) (for example, by coating and/or film fabrication), and the carriers may include, for example, particles and fibers.

The particles used here should preferably have the particle sizes of 1 to 1000 μm, particularly 10 to 350 μm, and as the material therefor, there may be preferably used, for example, diatmaceous earth, titanium dioxide, barium sulfate, zinc oxide, lead oxide, microcrystalline cellulose, silicious sand, glass, silica gel, crosslinked dextran, crosslinked polyacrylamide, agarose, crosslinked agarose, chitin, chitosan, various synthetic resins (e.g. polystyrene), but it is particularly preferable to use self-binding particles as disclosed in Japanese Unexamined Patent Publication Nos. 101760/1982 and 101761/1982. Typical examples of the material are shown in the following Table 3.

TABLE 3

| | Exemplary compounds: |
|---|---|
| (1) | Poly(styrene-co-glycidyl methacrylate) [90/10]. |
| (2) | Poly(styrene-co-methylacrylate-co-glycidyl methacrylate) [80/15/5]. |
| (3) | Poly(styrene-co-n-butyl methacrylate-co-glycidyl methacrylate) [75/15/10]. |
| (4) | Poly(styrene-co-vinyl benzyl chloride-co-glycidyl methacrylate) [80/10/10]. |
| (5) | Poly(styrene-co-divinylbenzene-co-glycidyl acrylate) [90/2/8]. |
| (6) | Poly(p-vinyltoluene-co-glycidyl methacrylate) [90/10]. |
| (7) | Poly(methacrylate-co-glycidyl methacrylate) [80/20]. |
| (8) | Poly(styrene-co-N,N—dimethylaminoethyl methacrylate) [95/5]. |
| (9) | Poly(styrene-co-aziridylethyl methacrylate) [95/5]. |
| (10) | Poly(styrene-co-methyl acrylate-co-acrolein) [90/5/5]. |
| (11) | Poly(styrene-co-acrylamide) [95/5]. |
| (12) | Poly(styrene-co-vinylthiol) [95/5]. |
| (13) | Poly(styrene-co-methylolated acrylamide) [95/5]. |
| (14) | Poly(styrene-co-t-butyl acrylate-glycidyl methacrylate) [90/5/5]. |
| (15) | Poly(styrene-co-vinylisocyanate) [95/5]. |
| (16) | Poly(methylacrylate-co-styrene-co-N—methylolacrylamide) [50/35/15]. |
| (17) | Poly(styrene-co-glycidyl methacrylate-co-N,N—dimethylaminoethyl methacrylate) [90/5/5]. |
| (18) | Poly(styrene-co-methacrylic acid-co-acrylamide) [95/2/3]. |
| (19) | Poly(styrene-co-N—methylolacrylamide-co-methoxyethyl acrylate) [90/5/5]. |
| (20) | Poly(p-vinyltoluene-co-N—methylolacrylamide-co-acrylic acid) [90/8/2]. |
| (21) | Poly(methyl methacrylate-co-glycidyl methacrylate-co-t-butyl acrylate) [80/10/10]. |
| (22) | Poly(styrene-co-p-vinylbenzyl chloride-co-acrylic acid-co-ureidoethyl acrylate) [75/10/5/10]. |
| (23) | Poly(styrene-co-methacrolein-co-α-hydroxyethyl methacrylate) [90/5/5]. |
| (24) | Poly(styrene-co-acrolein-co-acetoacetoxyethyl methacrylate) [85/5/10]. |
| (25) | Poly(styrene-co-N,N—dimethylaminoethyl acrylate-co-vinylsulfonylethyl methacrylate) [90/5/5]. |
| (26) | Poly(p-vinyltoluene-co-aminostyrene-co-vinylsulfonylethyl methacrylate) [85/10/5]. |
| (27) | Poly(styrene-co-N,N—dimethylaminoethyl methacrylate) [90/10]. |
| (28) | Poly(styrene-co-acrylic acid) [97/3]. |
| (29) | Poly(styrene-co-acrylamide) [97/3]. |
| (30) | Poly(p-vinyltoluene-co-t-butyl acrylate) [95/5]. |
| (31) | Poly(methyl acrylate-co-methacrylamide) [95/5]. |
| (32) | Poly(styrene-co-N—methylolacrylamide) [95/5]. |
| (33) | Poly(p-vinylbenzyl chloride-co-N—methylolacrylamide) [96/4]. |
| (34) | Poly(styrene-co-itaconic acid) [98/2]. |
| (35) | Poly(styrene-co-t-butyl acrylate) [92/8]. |
| (36) | Poly(methyl acrylate-co-styrene-co-acrolein) [30/65/5]. |
| (37) | Poly(methyl methacrylate-co-styrene-co-2-hydroxyethyl methacrylate) [25/70/5]. |
| (38) | Poly(styrene-co-vinylsulfonylethyl acrylate) [80/20]. |
| (39) | Poly(styrene-co-N,N—dimethylaminoethyl acrylate) [90/10]. |
| (40) | Poly(styrene-methyl acrylate-co-acetoacetoxyethyl acrylate) [90/5/5]. |
| (41) | Poly(styrene-co-methacrylic acid) [95/5]. |

The numerals in the parentheses after respective exemplary compounds show wt.% of the monomers used in polymerization reaction.

Alternatively, several kinds of these particles can be used as a mixture.

On the other hand, the fibers to be used in the porous reaction layer of the present invention may preferably be fibers of 40 to 400 mesh, including vegetable, animal, mineral, synthetic, semi-synthetic or regenerated fibers such as pulp (e.g. powdery filter paper), cotton, hemp, silk, wool, chitin, chitosan, cellulose ester, viscose rayon, cupraammonium rayon, polyamide (e.g. 6-nylon, 6,6-nylon, 6,10-nylon, etc.), polyester (e.g. polyethyleneterephthalate, etc.), polyolefin (polypropylene, vinylon, etc.), glass fiber, asbestos, etc. Alternatively these fibers may be used as a mixture.

Immobilization of a substance capable of specifically binding to said specific component can be accomplished by permitting said substance to be absorbed physically on the surface of the particles or fibers as described above or bound directly or indirectly by the chemical reaction according to various known methods. During immobilization, it is necessary to bear in mind that the specific bindability to said specific component of said substance should not be lost, and methods as described in, for example, "Enzyme Immunoassay (second edition)" edited by Ei ji Ishikawa, Tadashi Kawai, Kiyoshi Miyai (published by Igaku Shoin, 1978) or "Experiment and Application, Affinity Chromatography" written by Ichiro Chihata, Tetsuya Tosa and Yushi Matsuo (published by Kodansha, 1976) are examples of preferable methods.

Also, immobilization of said substances B and D onto the porous reaction layer may be effected to such an extent that the specific binding site is held and is not in the free state or dissolved state in a fluid sample, and they may be dispersed under insoluble state in a fluid sample. It is also possible to use the method used for dispersion of a coupler in color photography [for example, "Basis of Photographic Engineering, Volume of Silver Salt" edited by Photographic Society of Japan (published by Corona Co., 1978)], the method in which they are incorporated in lipid two molecular films, etc.

These immobilization operations may be previously practiced on the above particles or fibers before formation of the porous reaction layer, or alternatively it is also possible to form the porous reaction layer before practicing said immobilization operation.

In the case of the former, in addition to the particles or fibers having said substance (b) immobilized thereon and the particles or fibers having said substance D immobilized thereon, particles or fibers having only a protein which does not participate in the above mentioned specific reaction immobilized thereon can be also added for the purpose of control.

Also, for the purpose of precluding the non-specific reaction in the immune reaction, if desired, after immobilization of the substance B capable of specifically binding to said specific component A, it is possible to carry a protein which does not participate in the specific reaction to be assayed. Typical examples of such proteins may include, for example, normal serum proteins of mammals, albumin, gelatin and decomposed products thereof, etc.

According to the method as described above, the above carriers (a) and (b) are prepared. It is not necessarily required to use the same material for (a) and (b), but particles of different materials, fibers of different materials or combination of particles and fibers may be employed. However, for uniform mixing of (a) and (b), it is not desirable to combine particles with remarkably different mean particle sizes.

The mixing ratio of the particles or fibers of (a) and (b) is determined depending on the amount and the binding constant of the respective specific binding substances immobilized and, if desired, particles or fibers having no specific binding substance immobilized thereon can be further added for the purpose of control.

By coating and/or film fabrication of these mixtures, a porous reaction layer is formed in which a porous structure having mutually communicated voids permitting (a) and (b) and a fluid sample to contact freely with each other exists. Particles having no self-binding property can be fabricated into a film in the form in which the particles are mutually point adhered to each other with the use of an appropriate adhesive. For example, the method as disclosed in Japanese Unexamined Patent Publication No. 90859/1980 is applicable. Organic polymer particles having self-binding property can be similarly fabricated into a film according to the method as disclosed in Japanese Unexamined Patent Publication No. 101760/1982 or 101761/1982. For fibers or mixtures of fibers and particles, a porous reaction layer can be formed by coating of a fiber dispersion as disclosed in Japanese Unexamined Patent Publication No. 12584/1982, 197466/1982.

It is also possible to coat a fiber dispersion by use of a water-soluble binder such as gelatin or polyvinylpyrrolidone as in the method practiced in the specification of Japanese patent application No. 28571/1984.

The form of the analytical element of the present invention is not particularly limited, provided that it can perform analysis, but it is preferably in the form of a film or sheet from the viewpoint of preparation, operation and measurement.

In the present method, with respect to the substance B immobilized on the carrier (a) and the substance D immobilized on the carrier (b), a binding constant between the substance A and the substance B is preferably larger than a binding constant between the labelled material L and the absorbing substance D.

Further, in the sandwich method, a binding constant between the specific component A and the substance C is preferably larger than a binding constant between the labelled material L and the absorbing substance D.

In the competitive method, when a blank test (adding no the specific component onto the analytical element) is effected, it is preferable that 3 to 7 by weight % of the total labelled materials present in the reaction system of the analytical element bind to the substance B immobilized on the carrier (a) upon finishing of the analytical procedure.

For the improvement of precision in a practical analysis, that 0.1 to 10 by weight %, more preferably 0.1 to 5% of the total amount of the labelled material in the reaction system are kept in the free form or in the non-bound form is more preferrd to that all of the labelled materials which have not bound to the substance B are bound to the absorbing substance D.

For better understanding of the analytical element of the present invention, its priciple is explained by referring to an example.

FIG. 1 is an example of a sectional view of one of the most simple embodiments of the analytical element according to the present invention. In this case, the analytical element is constituted only of a porous reaction layer 1.

FIG. 2 is an enlarged view of FIG. 1. In FIG. 2, the symbol 2 shows the particles of the above (a), 3 the particles of the above (b) and 4 the particles added for the purpose of control.

FIG. 2 shows that a porous reaction layer is constituted by point adhesion of the particles 2, 3 and 4 according to uniform mixing.

FIG. 3-a is a schematic illustration of a labelled material $L_{comp}$ in the competitive reaction method, in which the symbol 7 means a specific component or its analogue in a fluid sample, 9 a label and 10 a labelled material $L_{comp}$.

FIG. 3-b is a schematic illustration of a labelled material $L_{sand}$, in which the symbol 8 means a substance which can be specifically bound to the specific component, 9 a label and 10 a labelled material $L_{sand}$.

FIGS. 4-a and 4-b are schematic illustrations of the competitive reaction method and the sandwich method in the present invention, respectively, in which the symbol 5 means a substance B which can be specifically bound to the specific component in a fluid sample, 6 an absorbing substance D and 7 a specific component A in the fluid sample.

The mechanism of the competitive reaction method or the sandwich method in the present invention is to be explained by referring to FIGS. 1, 2, 3-a, 3-b, 4-a and 4-b.

In the competitive reaction method, first, a predetermined amount of a fluid sample is weighed, mixed with a predetermined amount of the labelled material as mentioned above and added dropwise on the analytical element in FIG. 1.

The specific component A in the fluid sample and the labelled material $L_{comp}$ will react competitively with the "substance which can be bound specifically to the specific component in the fluid sample" B immobilized on the surface of the particles 2 in FIG. 2. Further, the labelled material $L_{comp}$ will also react with the absorbing substance D immobilized on the surface of the particles 3 (FIGS. 4-a).

In the sandwich method, a determined amount of a fluid sample is weighed and added dropwise on the analytical element in FIG. 1. The specific component in the fluid sample will be absorbed by the substance B which can be specifically bound to the specific component A in the fluid sample immobilized on the surface of particles or fibers.

Then, a solution containing the labelled material $L_{sand}$ ia added dropwise on the analytical element. The thus added labelled materials are partitioned between the specific component A absorbed on the surface of the particles of (a) and the absorbing substance E immobilized on the surface of the particles of (b) (FIG. 4-b).

In both methods, after a certain reaction time, the labelled material L exists under the three states, namely:
  (i) being absorbed onto the particles having the substance B which can be bound specifically to the specific component A in the fluid sample immobilized thereon through said substance B,
  (ii) being absorbed onto the particles having the absorbing substance D immobilized thereon, through said substance D, and
  (iii) remaining in the fluid sample. It is preferable to set the reaction conditions and the constitution of the porous reaction layer so that the proportion of (iii) among the above three states should be as small as possible. The proportion of (i) depends on the result of the competitive reactions of the specific component A and the labelled material L comp. in the fluid sample, and the proportion of (i) becomes lower and the proportion of (ii) higher as the concentration of said specific component A is higher. Since the labelled material under the state of (ii) is modulated in the signal caused by said label by binding between the labelled material and the absorbing substance D, a function relationship can be established between the concentration of the specific component A in the fluid sample and the signal intensity of the whole labelled material. Accordingly, if a calibration curve is prepared previously by use of several kinds of fluid samples of known concentrations of the specific component A (standard samples), the unknown concentration of the specific component in a fluid sample can be known therefrom.

Methods for adding the labelled material and the fluid sample containing the specific component are not particularly limited. Namely, the labelled material and the fluid sample containing the specific component may be added dropwise on the analytical element simultaneously, or the latter may be added first and then, after a predetermined period, the former may be added. Alternatively, they may be added in a different manner from described above, for example, by the use of a mixture of the fluid sample and the labelled material previously prepared. Although this method becomes disadvantageous in sensitivity to some extent, it is possible to facilitate the procedure of analysis extremely.

The method for measuring the signal differs depending on the kinds of the label. For example, when the label is a fluorescent substance, the fluorescent intensity may be measured by irradiating the analytical element with an exciting light. When the label is an enzyme, a solution containing an appropriate substrate and optionally an enzyme or a color developing system is added and incubated for a certain period of time, and the signal intensity can be measured by measuring the reflective density (fluorescent intensity, emission intensity depending on the kind of the substrate) of a light with a wavelength adopted to said color developing system. The substrate-color developing system can be selected suitably from the known methods depending on the kind of the label enzyme.

When enzymes are used as the labelled material L, there may preferably be used those of enzyme reaction type and those of color developing type in which hydrogen peroxide and NADH or NADHP are paticipated. The enzymes of enzyme reaction type in which hydrogen peroxide is participated may include the following:

| EC 1.1.3.1. | Glycolate oxidase, |
| --- | --- |
| 1.1.3.2. | Lactate oxidase, |
| 1.1.3.4. | Glucose oxidase, |
| 1.1.3.6. | Cholesterol oxidase, |
| 1.1.3.9. | Galactose oxidase, |
| 1.1.3.17. | Choline oxidase, |
| 1.1.3.-. | L-α-glycerophosphate oxidase, |
| 1.11.1.17. | Peroxidase, |
| 1.2.3.2. | Xanthine oxidase, |
| 1.2.3.3. | Pyruvate oxidase, |
| 1.2.3.4. | Oxalate oxidase, |
| 1.3.3.-. | Acyl CoA oxidase, |
| 1.4.3.2. | L-amino acid oxidase, |
| 1.4.3.3. | D-amino acid oxidase, |
| 1.4 3.6. | Amine oxidase (containing copper), |
| 1.5.3.1. | Sarcosine oxidase, |
| 1.7.3.3. | Urate oxidase, etc. |

Since the enzymes other than peroxidase are hydrogen peroxide generating enzymes, there may be used materials which convert the hydrogen peroxide generated into forms to be detectable (e.g. detection by colorimetry, fluorescence, emission, etc.) as exemplified by metal, e.g. platinum, silver, iron; and enzymes, e.g. peroxidase, catalase, etc.

To show an example, when the label is a peroxidase, it is possible to use a solution of one kind or several kinds of the compounds as exemplified in Table 4 dissolved in a buffer containing 0.001 to 10.0% of hydrogen peroxide (pH 4.0–9.0).

TABLE 4

| | |
|---|---|
| (1) | o-dianisidine |
| (2) | o-trydine or its acid salt |
| (3) | o-phenylenediamine or its acid salt |
| (4) | Guaiac wood |
| (5) | Adrenaline |
| (6) | Phenolphthalein |
| (7) | Ferrocyanide |
| (8) | Combination of 4-aminoantipyrine and its derivative or their acid salts with phenol or naphthol or their derivatives |
| (9) | Aniline and its derivatives |
| (10) | Monoamines such as o-toluidine, p-toluidine and the like |
| (11) | Diamines such as o-phenylenediamine, N,N'—dimethyl-p-phenylenediamine, N,N'—diethyl-phenylenediamine, benzidine, dianisidine and the like |
| (12) | Phenols such as phenol, thymol, o-, m- and p-cresol, $\alpha$-naphthol, $\beta$-naphthol and the like |
| (13) | Polyphenols such as catechol, guaiacol, orcinol, pyrogallol, p,p-dihydroxydiphenyl, fluoroglucinol |
| (14) | Aromatic acids such as salicylic acid, pyrocatechinic acid, gallic acid |
| (15) | Leuco dyes such as leucomalachite green, leucophenolphthalein |
| (16) | Coloring dyes such as 2,6-dichlorophenolindophenol |
| (17) | Various biochemical substances such as epinephrine, flavones, tyrosine, dihydroxyphenylalanine, tryptophan |
| •(18) | Special dyes such as 2,2'-azinodi(3-ethyl-6-sulfobenzothiazoline) or its salt, and 3,3'-diaminobenzidine |
| (19) | Otherwise, guaia gum, guaiaconic acid, potassium iodide, sodium iodide and other water-soluble iodides, and substances such as bilirubin |

In the case when the label is an enzyme substrate, a coenzyme, an apoenzyme, a substance for activating an enzyme precursor or an enzyme precursor, the same compound as listed in Table 4 can be applied. Thus, it is only required that a solution of a substance necessary for measurement of the signal may be added and incubated, followed by measurement of reflective density, fluorescent intensity, emission intensity, etc.

The particles or fibers of the carrier represented by the above (a) and (b) to be used in the present invention constitute the reaction layer with their surfaces aparted from each other except for slight adhered portions when observed microscopically. This ensures the space for housing the fluid sample and at the same time prevents the labelled material L absorbed on the material B immobilized on the surface of the particles or fibers of (a) from influence of the absorbing substance D immobilized on the surface of the particles or fibers of (b) to be modulated in its signal. As a result, it has been rendered possible to effect B/F separation within a single layer which is the specific feature of the present invention.

Further, as another effect of the present invention, it is possible to supply analytical elements having always constant performances by controlling the mixing ratio of (a) and (b), even if the amounts of the substances immobilized on (a) and (b) or the binding ability to the labelled material L may vary more or less from lot to lot produced, because the mixing ratio of the particles or fibers of (a), (b) and the particles or fibers of optionally added for the purpose of control can be freely set. In the analytical element utilizing a porous layer by use of a mass of particles or fibers of the prior art and products similar thereto, the mass of particles or fibers is dealt with merely as a vessel for housing a fluid sample. The attempt to perform B/F separation within a single layer by mixing the particles or fibers endowed with different functions constituting such a mass and fabricating the mixture into a film is entirely a new attempt and it was a surprising result entirely unexpected even to the present inventors that the effects as described above could be practically obtained.

The analytical element of the present invention has the porous reaction layer as described above as the minimum necessary constituent element, but various auxiliary layers can be provided in order to exhibit further the effect of the present invention. FIG. 5 to FIG. 10 show schematic sectional views showing one embodiment of the analytical element of the present invention, respectively.

The analytical element of the present invention shown in FIG. 5 has a porous reaction layer 1 laminated on a light-transmissive support 11, and handleability of the element is improved by the presence of the support. The support which can be used for such a purpose may include, for example, polymeric compounds such as cellulose acetate, polyethyleneterephthalate, polycarbonate and polyvinyl compounds (e.g. polystyrene) or transparent inorganic compounds such as glass. Said porous reaction layer may be directly coated and/or fabricated into a film on such a support, or alternatively the porous reaction layer may be formed once separately and then plastered on the above mentioned support. In the case of the enbodiment shown in FIG. 5, the fluid sample is required to be added dropwise from the side of the reaction layer, but it is possible to measure the signal from both sides.

In another embodiment shown in FIG. 6, a reaction layer is provided on a light reflective support 12. In this embodiment, both of dropwise addition of a sample and signal measurement are performed from the side of the porous reaction layer, and the light reflective support makes it easy to measure the signal by reflective density. (When the signal is measured by fluorescent intensity, a similar effect can be obtained by using similarly a black light-absorptive support.)

As the material of the support which can be used for such a purpose, there may be employed, in addition to the material of the support as mentioned above, ceramics, metals or papers applied with water-proof treatment such as resin coating, etc., and the above object can be accomplished by coating these materials with white pigments, etc., such as $TiO_2$, $BaSO_4$, mica, etc., or incorporating them in these materials, if desired.

The embodiment shown in FIG. 7 is also intended to the same purpose, and has a porous reaction layer 1 and a light reflective layer 13 successively laminated on a light-transmissive support 11. In this embodiment, the sample is added dropwise from the light reflective layer side, and signal measurement is performed from the light-transmissive support side. For the light reflective layer, any of those which have been used for known analytical elements and products similar thereto can be used, but preferably the same particles and fibers as used for the porous reaction layer, in which the white pigment, etc., as mentioned above is contained can be coated or formed into a film, or plastered on the reaction layer. More preferably, it is possible to provide a light reflective layer endowed with the same function as the porous reaction layer of the lower layer, by immobilizing a substance B which can be specifically bound to the specific component in a fluid sample or an absorbing substance D on the surface of the particles containing internally a white pigment similarly as employed for the porous reaction layer. By use of such a special light reflective layer, it is possible to prevent the light reflective layer from retaining much unaltered labelled material therein.

In the embodiment shown in FIG. 8, a labelled material-containing layer 14 is provided on a porous reaction layer 1. The labelled material-containing layer is a layer in which the labelled material is contained in the porous medium to a constant area density, and a constant amount of the labelled material is dissolved out by dropwise addition of a constant amount of a liquid sample to be diffused together with the sample into the porous reaction layer. As the material, the same material as that of the porous reaction layer may be coated, formed into a film or plastered. Alternatively, it is also possible to plaster a labelled material-containing layer made of a fabric, unwoven fabric or synthetic paper prepared from water-absorptive paper, Japanese paper, filter paper, brush polymer, or glass fiber, mineral fiber (asbestos, etc.), vegetable fiber (cotton, hemp, pulp, etc.), animal fiber (wool, silk, etc.), synthetic fiber (various nylon, vinylon, polyethyleneterephthalate, polypropylene, etc.), regenerated fiber (rayon, cellulose ester, etc.) and others singly or as a mixture. Also, if desired, the labelled material-containing layer can be also endowed with the effect of the light reflective layer as described above. In the case of the embodiment of FIG. 8, if the label is a fluorescent substance, only a fluid sample may be added dropwise and incubated, whereby measurement is immediately possible. When the label is another substance, after dropwise addition of a fluid sample, incubation is carried out for a certain period of time and then a solution containing necessary substrates, color developing reagent, etc., can be added dropwise to carry out measurement.

Figure 9:
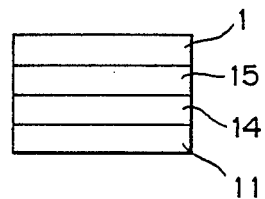

FIG. 9 shows also another embodiment having a labelled material-containing layer. In this case, a light-transmissive support 11, a labelled material-containing layer 14, a timing layer 15 and a porous reaction layer 1 are successively laminated from below.

Provision of the timing layer is based on a technique which is widely known in the field of photographic chemistry and, for example, gelatin layer controlled to a suitable film hardness is used. In this embodiment, after dropwise addition of a fluid sample, the labelled material is released into the porous reaction layer after the specific component in the sample is adsorbed to some extent on the surface of the corresponding particles in the porous reaction layer. Such a method is widely known as delayed addition and is effective for detection of a minute amount of a component.

In the case when the labelled material-containing layer exists in the portion other than the uppermost layer as in this embodiment, as the material to be used for the labelled material-containing layer, in addition to those as mentioned above, there may be employed a coating of a continuous binder, including hydrophilic polymeric materials such as gelatin, gelatin derivatives, polysaccharides (e.g. agarose, etc.), carboxymethyl cellulose, hydroxyethyl cellulose, etc., or homopolymers or copolymers of such monomers as vinylpyrrolidone, acrylic acid derivatives, methacrylic acid derivatives, vinyl alcohol, sulfonylstyrene, etc. As still another embodiment, the labelled material-containing layer can be also endowed with the function of the timing layer by controlling the film thickness and the composition of such a hydrophilic polymeric material or a polymer, thereby controlling the speed of the labelled material dissolved out from the labelled material-containing layer.

Figure 10:
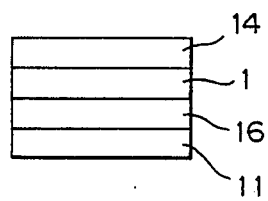

The embodiment shown in FIG. 10 is particularly useful when the label is other than a fluorescent substance (in the case of a label utilizing an enzymatic reaction in some form in measuring the signal). The reagent layer 16 is of the same material as in the labelled material-containing layer 14, and the substances necessary in measuring the label signal are contained to a constant area concentration therein. By providing the reagent layer and the labelled material-containing layer, even when employing a label other than a fluorescent substance, measurement becomes possible by only adding dropwise a fluid sample followed by incubation.

In this case, the contents in the reagent layer should preferably be dissolved out after the reaction in the porous reaction layer has sufficiently proceeded, and for that purpose, it is necessary to provide a timing layer as described above on the reagent layer or alternatively to impart the effect of a timing layer to the reagent layer by controlling its composition. Also, for the same reason, it is preferable to provide the reagent layer at the lowest layer of the analytical element, when there is a support, on the support.

The color developing reagent layer comprises at least one layer of a hydrophilic colloid containing a substrate and color developing reagents necessary during assay of enzyme activity.

In the analytical element according to the present invention, the substrate and color developing reagents can be formed into a coating liquid by dissolving or dispersing them in a binder comprising a hydrophilic colloid. Particularly, for dispersion of a hydrophobic compound, there may be employed various known dispersing methods such as the oil protect dispersing method, the direct dispersing method, etc., which have been frequently used in the field of photographic business.

Further, the hydrophilic colloid to be used in the color developing reagent layer according to the present invention may include gelatin, gelatin derivatives such as phthalated gelatin, etc., synthetic polymers such as polyvinyl alcohol, polyvinylpyrrolidone, polyvinylimidazole, polyacrylamide, polysodium acrylate, etc., polysaccharide as exemplified by cellulose derivatives such as hydroxyethyl cellulose, carboxymethyl cellulose sodium salt, etc. Preferably, gelatin and gelatin derivatives such as phthalated gelatin may be employed.

Further, the binder in the color developing reagent layer according to the present invention may be substituted partially with another water-dispersible polymer, namely a polymer latex for improvement of its film properties such as swelling degree or melting characteristic with heat. Examples of preferable polymer latices may include those disclosed in Japanese Patent Applications Nos. 1931/1981 and 177596/1981 as useful ones. The polymer latices can substitute 70% of the hydrophilic colloid binder at maximum but preferably the substitution degree may be about 55% or less.

In the color developing reagent layer, other additives such as buffering agents, preservatives, film hardeners, surfactants, mordants, etc., can be added depending on the purpose.

Its film thickness may be about 3 to about 50 μm preferably about 5 to 30 μm.

Buffering agents are used for controlling pH suitably for the specific binding reaction, the enzyme reaction, the color developing reaction, etc. Examples of useful buffering agents are disclosed in "Chemical Handbook, Basic Volume" edited by Chemical Society of Japan [published by Maruzen K. K., 1966], P. 1312-1320; N. E. Good et al, Biochemistry, Vol. 5, P. 467 (1966); Imamura, Saito, Domain of Chemistry, Vol. 30 (2), P. 79 (1976); W. J. Ferguson et al, Analytical Biochemistry (Anal. Biochem.), Vol. 104, P. 300 (1980), etc. Specific examples may include boric acid salts, phosphoric acid salts, carbonic acid salts, tris, barbital, glycine, Good buffering agents, etc. These buffering agents may be also contained in the layer other than the color developing reagent layer, if necessary.

Preservatives are contained for storage stabilization of substrates and color developing reagents and may include antioxidant agents, etc.

Also, not only in the present reagent layer, but also for maintenance of activities of the substances B and D immobilized in all the layers and the labelled material L, there may be contained preservatives which can be used for storage of immobilized enzymes, adsorbents for affinity chromatography, immobilized antibodies and proteins or enzymes, etc. The materials for such preservatives may include those as disclosed in "Biochemical Experimental Course 1, Chemistry of Protein I" edited by Biochemical Society of Japan (published by Tokyo Kagaku Dojin K. K., 1976), P. 66-67; "Experiment and Application of Affinity Chromatography", supra, P. 103-104; Japanese Unexamined Patent Publication No. 149927/1985, etc.

Specific examples may include gelatin, decomposed products of gelatin, albumin, BSA, cyclodextrins, non-reducing sugars (sucrose, trehalose), polyethyleneglycol, amino acids, various ions, sodium azide etc. These preservatives should preferably be permitted to exist in the vicinity of the immobilized substances B and D and the labelled material L.

As the film hardener, substances frequently used in the field of photographic business can be used, including those as described in "The Theory of the Photographic Process" (fourth edition), edited by T. H. James, P. 77-87. Specific examples may include aldehydes, active olefins, active esters, etc.

As the surfactant, those as described above may be employed. Other reagents which may be contained in the layer may include dissolving aids, Blocker reagents, etc. These additives may be added in appropriate amounts, if necessary.

Mordants are substances for collecting concentratedly the detecting substance for assay of enzyme activity in the color developing reagent layer, for enhancing light absorption coefficient or shifting the wavelength when the detecting substance is a dye, exhibiting strong mutual interaction with the detecting substance.

Cationic polymers, anionic polymers and latices of these polymers may be employed.

When a peroxidase is used in the enzymatic reaction system, hydrogen peroxide as the substrate and an appropriate reducing substance are required. Of these, since the former is volatile, it can be contained as such in the element with difficulty and therefore it is preferable that it should be contained in the form of cumene. $H_2O_2$, or hydrogen peroxide should be generated when the fluid sample is added dropwise. The latter can be accomplished by incorporating into the reagent layer an oxidase (of the type forming hydrogen peroxide as the reaction product) as exemplified typically by glucose oxidase, uric acid oxidase, amine oxidase and a substrate for the enzyme in the dry state, or alternatively by incorporating one of said oxidase and substrate in the reagent layer and the other in a layer different therefrom.

Figure 11:
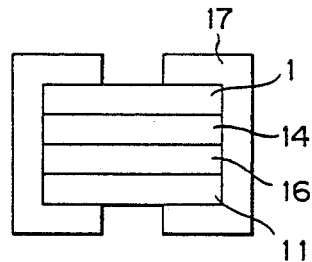
FIG. 11 is a sectional view of one preferred embodiment of the present invention.
Figure 12:
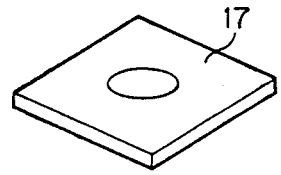
FIG. 12 is a perspective view of FIG. 11.

FIG. 11 and FIG. 12 shows a sectional view and a perspective view respectively of a preferred embodiment of the present invention. For enabling easy handling of the analytical element, the element as a whole is covered with a mount 17 made of plastic and a hole for injecting sample is opened at the upper portion of the mount and a hole for measuring the signal opened at the lower portion of the mount.

The analytical element of the present invention can further provide auxiliary layers such as a spreading layer for asisting in spreading of a fluid sample when applied to the element, a blood cell separating layer which may become necessary when the fluid sample is a blood (whole blood), an adhesive layer which is provided if necessary, or a protective layer. These auxiliary layers and the color developing reagent layer, the labelled material-containing layer and the timing layer as described above may be provided either independently, or alternatively as a layer having a plural number of functions in combination. The positions where these layers are to be provided can be determined easily depending on their functions.

The present invention is described in more detail by referring to Examples, but the present invention is not limited at all by these Examples.

EXAMPLE 1

(1) Preparation of rabbit anti-FITC antibody

To a solution of 50 mg of bovine serum albumin (BSA) dissolved in 5 ml of 0.1 mol sodium carbonate solution (pH 9.0) was added a solution of 2 mg of fluorescein isothiocyanate (produced by Research Organics Co., U.S.A.) dissolved in 500 μl of dimethylformamide, and the mixture was stirred at room temperature under the state shielded from light for 3 hours and purified through Sephadex G-25 column (produced by Pharmacia Co.), followed by lyophilization.

The product was mixed with Freund's complete adjuvant (only in the first immunization) and incomplete adjuvant and used for immunization of rabbit.

Globulin fractions were separated from the antiserum obtained according to the ammonium sulfate method, and the antibodies adsorbed on BSA were removed by affinity chromatography, followed by dialysis and lyophilization.

(2) Preparation of porous reaction layer (a) To a solution of a goat anti-human IgG (produced by Cappel Co., U.S.A) dissolved at a concentration of 10 μg/ml in B 0.05M carbonate-bicarbonate buffer of pH B 9.6 were added polymer particle units of a poly(styrene-co-n-butyl methacrylate-co-glycidyl acrylate) [75/15/10] with a mean particle size of 21 μm, and the mixture was left to stand at 4° C. overnight. After the particles were washed with physiological saline, they were placed into a similar buffer containing 200 μg/ml of BSA and left to stand at 4° C. for 3 days, followed by washing with physiological saline.

(b) The same operation as in (a) was performed except for using the anti-FITC antibody prepared in (1) in place of the anti-human IgG.

(c) According to the method similar to (a), particles having only BSA physically adsorbed thereon were prepared.

The particles prepared in the above (a)-(c) were uniformly mixed at a ratio of 4:1:5, and the mixture together with 5 wt.% of Triton X-100 (a nonionic surfactant, produced by Rohm & Haas Co.) was applied on a polyethyleneterephthalate support so that a dried film thickness may be about 350 μm, followed by drying at 42° C. for 30 minutes. The film thus formed was peeled off from the support.

(3) Preparation of a labelled material-containing layer

On a polyethyleneterephthalate film applied with subbing treatment, a reagent layer having the following composition was prepared by coating and drying.

| | |
|---|---|
| FITC labelled human IgG (produced by Cappel Co., U.S.A. | 2.8 mg/m² |
| Na₂HPO₄ · 2H₂O | 0.72 g/m² |
| NaH₂PO₄ · H₂O | 0.13 g/m² |
| Deionized gelatin | 16.00 g/m² |
| Bisvinylsulfonylmethyl ether | 0.04 g/m² |

(4) Preparation of analytical element

On the labelled material-containing layer prepared in (3), the porous reaction layer prepared in (2) was adhered, and the composite was cut into a size of 2×2 cm to provide an analytical element.

(5) Assay of human IgG

Various 0.01M sodium phosphate buffers (pH 7.6) contaning human IgG (produced by Cappel Co., U.S.A.) at various concentrations 640 μg/ml to 0 μg/ml were prepared.

Each 10 μl of human IgG solutions of various concentrations was added dropwise on each one sheet of the analytical element prepared in (4) and after incubation at 37° C. for 20 minutes, fluorescence was measured (excitation wavelength 490 n, fluorescent wavelengh 520 nm) from the side on which the sample was added to obtain the results as shown in Table 5.

TABLE 5

| Human IgG concentration (μg/ml) | Fluorescence intensity (arbitrary unit) |
|---|---|
| 0 | 151 |
| 5 | 136 |
| 10 | 119 |
| 20 | 101 |
| 40 | 85 |
| 80 | 68 |
| 160 | 52 |
| 320 | 36 |
| 640 | 23 |

EXAMPLE 2

(1) Preparation of reagent layer

On a film of polyethyleneterephthalate applied with subbing treatment, a color developing reagent layer having the following composition was prepared by coating and drying.

| | |
|---|---|
| Glucose | 0.80 g/m² |
| O—phenylenediamine | 0.40 g/m² |
| Citric acid | 0.16 g/m² |
| Disodium phosphate | 0.23 g/m² |
| Deionized gelatin | 16.00 g/m² |
| Bisvinylsulfonylmethyl ether | 0.06 g/m² |

(2) Preparation of a labelled material-containing layer

On the reagent layer prepared in (1), a layer containing the following labelled material was prepared by coating and drying.

| | |
|---|---|
| Peroxidase labelled human IgG (produced by Cappel Co., U.S.A.) | 8.4 mg/m² |
| Na₂HPO₄ · 2H₂O | 0.72 g/m² |
| NaH₂PO₄ · H₂O | 0.13 g/m² |
| Deionized gelatin | 16.00 g/m² |
| Bisvinylsulfonylmethyl ether | 0.04 g/m² |

(3) Introduction of reactive groups into cellulose fiber

An amount of 55 g of powdery filter paper D (produced by Toyo Roshi Co.) was immersed in 1000 ml of 2.5M potassium phosphate buffer (ph 12.1) and, under stirring by means of a stirre at 5° to 10° C., 500 ml of a bromocyan solution (0.05 g/ml) was gradually added thereto. After the reaction for 20 minutes, the product was filtered and washed successively with ice-cooled distilled water and 0.1M sodium hydrogen carbonate.

(4) Preparation of porous reaction layer (a) To a solution of 1.0 mg of IgG fraction (calculated on antibody protein) of a goat anti-human IgG (produced by Cappel Co., U.S.A.) dissolved in 40 ml of 0.1M NaHCO₃–0.5M NaCl solution was charged a part of the activated filter paper prepared in (3), followed by shaking at room temperature for 3 hours. After filtration, the product was shaked together with 1M trishydrochloride buffer (pH 8.0) at room temperature for 2 hours. The mixture was successively washed with water, 0.5M acetate buffer (pH 4.0), 0.5M NaHCO₃, 50 mM phosphate-buffered physiological saline (pH 7.2). This is immersed overnight in 50 mM tris-hydrochloride buffer (pH 8.0) containing 2% BSA, then washed with distilled water and a small amount of an aqueous solution of BSA and sucrose was incorporated before lyophilization.

(b) A part of the activated filter paper prepared in (3) was allowed to react with o-dianisidine at pH 9 in a dark place at room temperature overnight. After filtration, the reaction product was treated with 1M 1-amino-2-propanol, washed with water and then subjected to BSA treatment similarly in (a), followd by drying.

(c) By use of glucose oxidase and a part of the activated filter paper prepared in (3), the same operation as in (a) was conducted.

By use of the three kinds of treated fibers as described above, a fiber dispersion having the following composition was prepared and applied on the layer containing the labelled-material prepared in (2), followed by drying.

| | |
|---|---|
| Treated fiber (a) | 1 g |
| Treated fiber (b) | 3 g |
| Treated fiber (c) | 1 g |

-continued

| | |
|---|---|
| Poly(styrene-co-glycidyl methacrylate) [90/10] | 0.75 g |
| Octylphenoxypolyethoxyethanol | 0.5 g |
| Xylene | 14 ml |

After drying, the composite was cut into a size of 2×2 cm to provide an analytical element.

(5) Assay of human IgG

Various 0.01M sodium phosphate buffers (pH 7.6) containing human IgG (produced by Cappel Co., U.S.A.) at various concentrations from 640 μg/ml to 0 μg/ml were prepared.

Each 10 μl of human IgG solutions of various concentrations was added dropwise on each one sheet of the analytical element prepared in (4) and after incubation at 37° C. for 20 minutes, the reflection density at 492 nm was measured from the support side. The results are shown in Table 6.

TABLE 6

| Human IgG concentration (μg/ml) | Reflection density |
|---|---|
| 0 | 1.36 |
| 5 | 1.28 |
| 10 | 1.13 |
| 20 | 1.00 |
| 40 | 0.83 |
| 80 | 0.66 |
| 160 | 0.48 |
| 320 | 0.36 |
| 640 | 0.30 |

As described above, according to the analytical element of the present invention, by performing B/F separation within a single layer, there can be brought about a remarkable effect that a specific component having a molecular weight of a wide range in a fluid sample can be quantitatively analyzed with good sensitivity, precision and reproducibility according to a simple operation.

EXAMPLE 3

(1) Preparation of porous reaction layer

The particles prepared in the above (a)–(c) of Example 1 were uniformly mixed at a ratio of 7:1:3, and the mixture together with 5wt.% of Triton X-100 (a nonionic surfactant, produced by Rohm & Haas Co.) was applied on a polyethyleneterephthalate support so that a dried film thickness may be about 350 μm, followed by drying at 42° C. for 30 minutes. The film thus formed was peeled off from the support.

(2) Preparation of a labelled material-containing layer

On a polyethyleneterephthalate film applied with subbing treatment, a reagent layer having the following composition was prepared by coating and drying.

| | |
|---|---|
| FITC labelled rat anti-human IgG (produced by Cappel Co., U.S.A. | 3.5 mg/m² |
| Na₂HPO₄ · 2H₂O | 0.72 g/m² |
| NaH₂PO₄ · H₂O | 0.13 g/m² |
| Deionized gelatin | 16.00 g/m² |
| Bisvinylsulfonylmethyl ether | 0.04 g/m² |

(3) Preparation of analytical element

On the labelled material-containing layer prepared in (2), the porous reaction layer prepared in (1) was adhered, and the composite was cut into a size of 2×2 cm to provide an analytical element.

(4) Assay of human IgG

Various 0.01M sodium phosphate buffers (pH 7.6) containing human IgG (produced by Cappel Co., U.S.A.) at various concentrations from 640 μg/ml to 0 μg/ml were prepared.

Each 10 μl of human IgG solutions of various concentrations was added dropwise on each one sheet of the analytical element prepared in (3) and after incubation at 37° C. for 20 minutes, the reflection density at 492 nm was measured from the support side. The results are shown in Table 7.

TABLE 7

| Human IgG concentration (μg/ml) | Fluorescence intensity (arbitrary unit) |
|---|---|
| 0 | 8 |
| 5 | 11 |
| 10 | 14 |
| 20 | 25 |
| 40 | 41 |
| 80 | 60 |
| 160 | 74 |
| 320 | 26 |
| 640 | 90 |

EXAMPLE 4

(1) Preparation of a labelled material-containing layer

On the reagent layer prepared in (1) of Example 2, a layer containing the following labelled material was prepared by coating and drying.

| | |
|---|---|
| Peroxidase labelled rat anti-human IgG (produced by Cappel Co., U.S.A.) | 10.5 mg/m² |
| Na₂HPO₄ · 2H₂O | 0.72 g/m² |
| NaH₂PO₄·H₂O | 0.13 g/m² |
| Deionized gelatin | 16.00 g/m² |
| Bisvinylsulfonylmethyl ether | 0.04 g/m² |

(2) Preparation of porous reaction layer

By the use of the three kinds of treated fibers as described in Example 2, a fiber dispersion having the following composition was prepared and applied on the layer containing the labelled-material prepared in (1), followed by drying.

| | |
|---|---|
| Treated fiber (a) | 2.5 g |
| Treated fiber (b) | 2.0 g |
| Treated fiber (c) | 0.5 g |
| Poly(styrene-co-glycidyl methacrylate) [90/10] | 0.75 g |
| Octylphenoxypolyethoxyethanol | 0.5 g |
| Xylene | 14 ml |

After drying, the composite was cut into a size of 2×2 cm to provide an analytical element.

(3) Assay of human IgG

Various 0.01M sodium phosphate buffers (pH 7.6) containing human IgG (produced by Cappel Co., U.S.A.) at various concentrations from 640 µg/ml to 0 µg/ml were prepared.

Each 10 µl of human IgG solutions of various concentrations was added dropwise on each one sheet of the analytical element prepared in (2) and after incubation at 37° C. for 20 minutes, the reflection density at 492 nm was measured from the support side. The results are shown in Table 8.

TABLE 8

| Human IgG concentration (µg/ml) | Reflection density |
|---|---|
| 0 | 0.45 |
| 5 | 0.48 |
| 10 | 0.51 |
| 20 | 0.63 |
| 40 | 0.76 |
| 80 | 0.84 |
| 160 | 0.91 |
| 320 | 0.96 |
| 640 | 1.10 |

As described above, according to the analytical element of the present invention, by performing B/F separation within a single layer, there can be brought about a remarkable effect that a specific component having a molecular weight of a wide range in a fluid sample can be quantitatively analyzed with good sensitivity, precision and reproducibility according to a simple operation.

We claim:

1. An analytical element for determining a specific component A in a test sample, based on the specific reaction between said specific component A and a substance B capable of binding specifically to said specific component A, by the use of a labelled material L comprising a label capable of providing a signal and said specific component A, wherein said element has a porous reaction layer forming a mixture of (a) a carrier having immobilized substance B and (b) a carrier having an immobilized absorbing substance D capable of binding specifically to the label of said labelled material L which has not bound to said substance B, to thereby modulate said signal.

2. The analytical element according to claim 1, wherein the substance B is selected from the group consisting of an antibody, an antigen, a lectin, a protein A and an enzyme inhibitor.

3. The analytical element according to claim 2, wherein the substance B is an antibody or an antigen.

4. The analytical element according to claim 1, wherein combination of said label and said absorbing substance D is selected from the group consisting of an enzyme and an inhibitor for the enzyme; a coenzyme or a prosthetic group and an antibody; an apoenzyme and a prosthetic group; an enzyme precursor and a substance capable of making the enzyme to develop the activity thereof; and a fluorescent substance and an antibody against the fluorescent substance.

5. The analytical element according to claim 4, wherein the inhibitor in the combination of an enzyme and an inhibitor for the enzyme is an organic mercury compound.

6. The analytical element according to claim 1, wherein said carrier is particles or fibers.

7. The analytical element according to claim 6, wherein said particles have a particle size of 1 to 1,000 µm.

8. The analytical element according to claim 6, wherein said fibers are ones selected from the group consisting of pulp, cotton, hemp, silk, wool, chitin, chitosan, cellulose ester, viscose rayon, cupraammonium rayon, polyamide, polyester, polyolefin, glass fiber and asbestos.

9. The analytical element according to claim 6, wherein said fibers are ones of 40 to 400 mesh.

10. Th analytical element according to claim 1, wherein said element additionally contains a regent layer.

11. The analytical element according to claim 1, wherein said element additionally contains a timing layer.

12. An analytical method for determining a specific component A in a test fluid sample in a single layer, by employing an analytical element based on the specific reaction between said specific component A and a substance B capable of binding specifically to said specific component A, by the use of a labelled material L comprising a label capable of providing a signal and said specific component A, said element having a porous reaction layer containing a mixture of (a) a carrier having immobilized substance B and (b) a carrier having an immobilized absorbing substance D capable of binding specifically to the label of said labelled material L which has not bound to said substance B, to thereby modulate said signal, the method comprising the steps of:

(a) adding said test fluid sample containing said specific component A, and said labelled material L onto said analytical element, and (b) after a predetermined period of reaction time, measuring said modulated signal as a function of said specific component in said test fluid sample.

13. The analytical method according to claim 12, wherein the method comprises the steps of:

(a) mixing a predetermined amount of said test fluid sample containing said specific component A with a predetermined amount of said labelled material L, (b) adding dropwise the thus prepared mixture to said analytical element, and (c) after a predetermined period of reaction time, measuring said modulated signal as a function of said specifical component A in said test fluid sample.

14. An analytical element for determining a specific component A in a test sample, based on the specific reaction between said specific component A and substance B capable of binding specifically to said specific component A, by the use of a labelled material L comprising a label capable of providing a signal and a substance C capable of binding specifically to said specific component A, wherein said element has a porous reaction layer containing a mixture of (a) a carrier having immobilized B and (b) a carrier having an immobilized absorbing substance D capable of binding specifically to the label of said labelled material L which has not bound to said specific component A, to thereby modulate said signal.

15. The analytical element according to claim 14, wherein the substance B is selected from the group consisting of an antibody, an antigen, a lectin, a protein A and an enzyme inhibitor.

16. The analytical element according to claim 15, wherein the substance B is an antibody or an antigen.

17. The analytical element according to claim 14, wherein combination of said label and said absorbing substance D is selected from the group consisting of an enzyme and an inhibitor for the enzyme; a coenzyme or a prosthetic group and an antibody; an apoenzyme and a prosthetic group; an enzyme precursor and a substance capable of making the enzyme to develop the activity thereof; and a fluorescent substance and an antibody against the fluorescent substance.

18. The analytical element according to claim 17, wherein the inhibitor in the combination of an enzyme and an inhibitor for the enzyme is an organic mercury compound.

19. The analytical element according to claim 14, wherein said carrier is particles or fibers.

20. The analytical element according to claim 19, wherein said particles have a particle size of 1 to 1,000 μm.

21. The analytical element according to claim 20, wherein said fibers are ones selected from the group consisting of pulp, cotton, hemp, silk, wool, chitin, chitosan, cellulose ester, viscose rayon, cupraammonium rayon, polyamide, polyester, polyolefin, glass fiber and asbestos.

22. The analytical element according to claim 19, wherein said fibers are ones of 40 to 400 mesh.

23. The analytical element according to claim 14, wherein said element additionally contains a reagent layer.

24. The analytical element according to claim 14, wherein said element additionally contains a timing layer.

25. An analytical method for determining a specific component A in a test fluid sample in a single layer, by employing an analytical element based on the specific reaction between said specific component A and a substance B capable of binding specifically to said specific component A, by the use of a labelled material L comprising a label capable of providing a signal and a substance C capable of binding specifically to said specific component A, said element having a porous reaction layer containing a mixture of (a) a carrier having immobilized substance B and (b) a carrier having an immobilized absorbing substance D capable of binding specifically to the label of said labelled material L which has not bound to said specific component A, to thereby modulate said signal, the method comprising the steps of:
(a) adding said test fluid sample containing said specific component A, and said labelled material L onto said analytical element, and
(b) after a predetermined period of reaction time, measuring said modulated signal as a function of said specific component in said test fluid sample.

26. The analytical method according to claim 25, wherein the method comprises the steps:
(a) adding a predetermined amount of said test fluid sample containing said specific component A to said analytical element,
(b) then, after a predetermined period of reaction time, adding a predetermined amount of said labelled material to said analytical element, and
(c) after a predetermined period of reaction time, measuring said modulated signal as a function of said specific component A in said test fluid sample.

* * * * *

UNITED STATES PATENT AND TRADEMARK OFFICE
CERTIFICATE OF CORRECTION

PATENT NO. : 4,868,106
DATED : September 19, 1989
INVENTOR(S) : Tsukasa Ito et al.

It is certified that error appears in the above-identified patent and that said Letters Patent is hereby corrected as shown below:

Claim 1, column 31, line 37, change "forming" to --containing--.

Claim 10, column 32, line 8, change "regent" to --reagent--.

Claim 10, column 32, line 7, change "Th" to --The--.

Claim 14, column 32, line 56, change "immobilized B" to --immobilized substance B--.

Claim 21, column 33, line 17, change "Claim 20" to --Claim 19--.

Signed and Sealed this

Twenty-seventh Day of August, 1991

Attest:

HARRY F. MANBECK, JR.

Attesting Officer

Commissioner of Patents and Trademarks